United States Patent [19]

Kaufman

[11] 4,416,291
[45] Nov. 22, 1983

[54] MULTIPLE SAMPLE NEEDLE ASSEMBLY WITH VEIN ENTRY INDICATOR

[75] Inventor: Joseph Kaufman, Emerson, N.J.

[73] Assignee: Becton Dickinson and Company, Paramus, N.J.

[21] Appl. No.: 284,894

[22] Filed: Jul. 20, 1981

[51] Int. Cl.³ .............................................. A61B 5/14
[52] U.S. Cl. .................................. 128/766; 128/763; 128/764
[58] Field of Search .................... 128/760, 763–768

[56] References Cited

U.S. PATENT DOCUMENTS

| | | | |
|---|---|---|---|
| 3,200,813 | 8/1965 | Cristakis | 128/764 X |
| 3,469,572 | 9/1969 | Nehring | 128/764 |
| 3,874,367 | 4/1975 | Ayres | 128/766 |
| 3,886,930 | 6/1975 | Ryan | 128/766 X |
| 4,207,870 | 6/1980 | Eldridge | 128/766 |

Primary Examiner—Kyle L. Howell
Assistant Examiner—John C. Hanley

[57] ABSTRACT

A multiple sample needle assembly useful in collecting liquid samples from a source comprises a housing with a chamber therein. A first cannula is in fluid communication with the chamber and is adapted for insertion into a liquid source. A second cannula is also in fluid communication with the chamber and is adapted to deliver liquid passing through the chamber to a liquid collector. A gas-permeable, liquid-impermeable porous member is positioned in the lumen of the second cannula. The second cannula preferably includes at least one side hole and an operable valve for collecting liquid from the second cannula by diverting liquid flowing therethrough away from the liquid-impermeable member.

13 Claims, 9 Drawing Figures

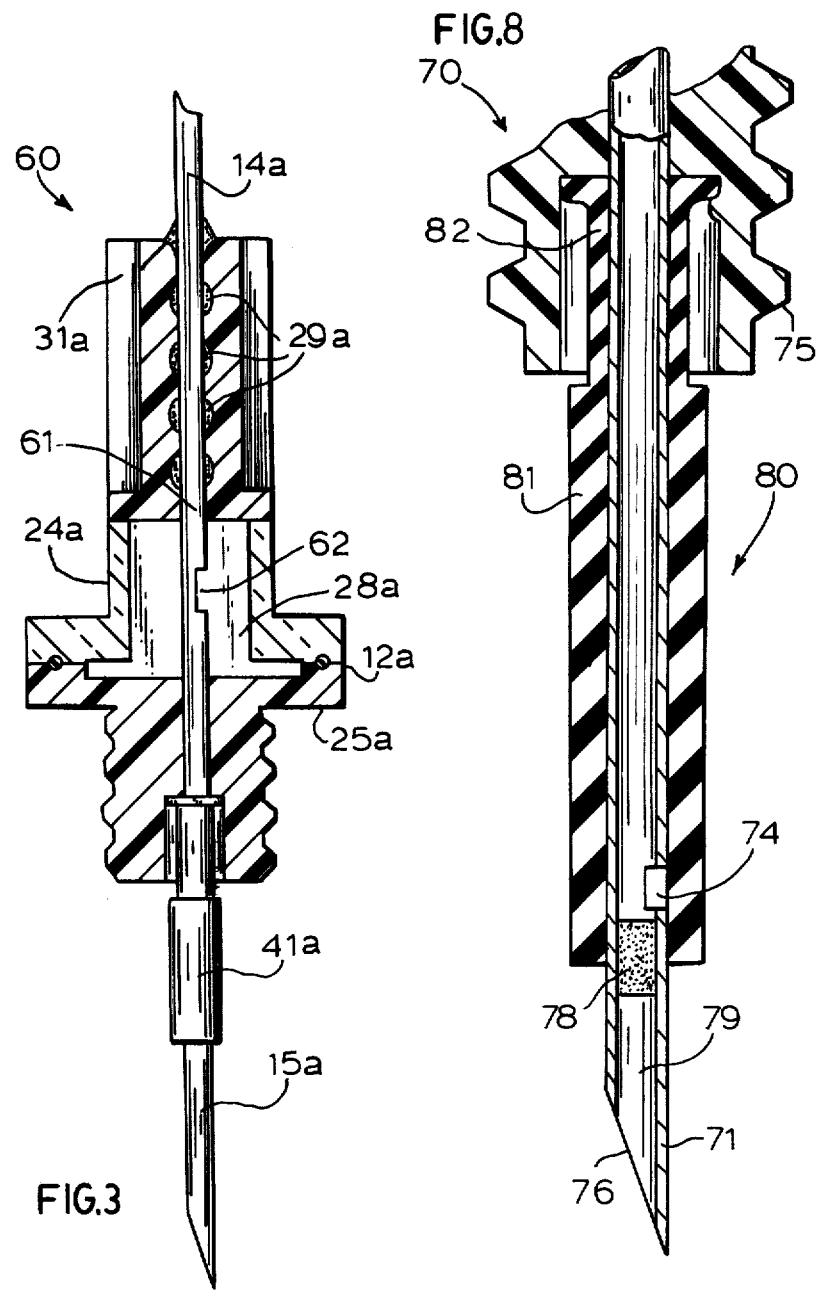

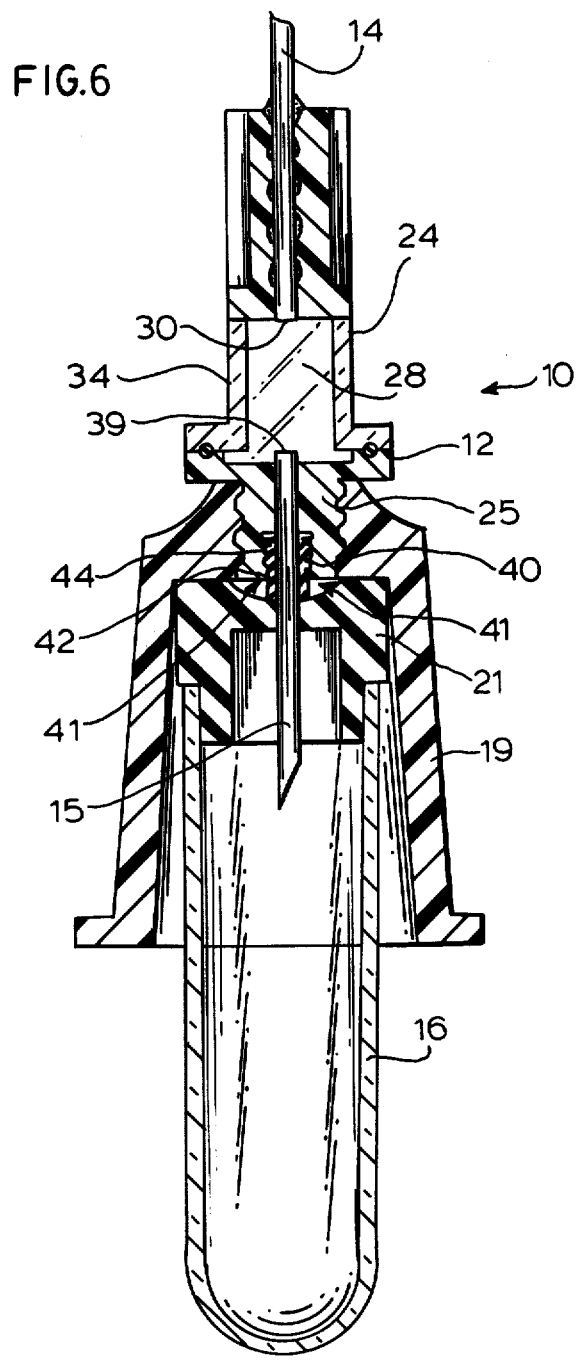

MULTIPLE SAMPLE NEEDLE ASEMBLY WITH VEIN ENTRY INDICATOR

BACKGROUND OF THE INVENTION

1. Field of the Invention

The present invention relates to a needle assembly for collecting fluid such as from a patient, and more particularly, concerns a needle assembly for collecting multiple samples of blood from a patient into evacuated tubes without leaking blood while the tubes are being changed, and with a provision for indicating the entry of the needle assembly into the vein of the patient.

2. Description of the Prior Art

It is now standard practice to collect multiple samples of fluid, such as blood, from a patient in a single procedure. Once the needle is inserted into the vein of the patient, successive evacuated blood collection tubes are inserted into a holder which is connected to the needle and is adapted to receive these evacuated tubes therein. As each filled tube is removed from the holder, the needle remains inserted in the patient's vein. Various valves are now in use which prevent blood from flowing out of the holder during the time between removal of the filled tube and insertion of the next evacuated tube for collection of the subsequent sample. Elastomeric sleeves over an interior needle commonly serve this valve purpose. It is appreciated that, while the known valves for multiple sample needle assemblies perform satisfactorily, different ways are being sought to provide improvements in these devices.

In addition, it is also desirable to provide a mechanism whereby the user of a multiple sample needle assembly can be informed when the intravenous needle has entered the vein of the patient. Many times in collecting blood from a patient it is difficult to locate the vein or for other reasons blood flow into the collection device is minimal. In these instances, it becomes most advantageous to be able to make a quick determination that entry into the vein has been made and that blood is flowing into the needle assembly. Once this determination has been made and vein entry indeed accomplished, the evacuated blood collection container can then be inserted into the collection assembly in accordance with these well known techniques of collecting multiple blood samples during a single collection procedure.

One of the problems which arises during the venipuncture step concerns the pocket of air which is found in various needle assemblies useful for multiple sample blood collections. When venipuncture is made, and the evacuated blood collection container is not yet attached to the opposite end of the needle structure, blood cannot always flow into the needle assembly because of this pocket of air which, under normal atmospheric conditions, remains inside the needle assembly. Accordingly, even though vein entry may have been accomplished, the blood may not move through the intravenous needle into the collection assembly under tourniquet pressure until the evacuated blood collection container is attached, whereupon the vacuum force causes sufficient draw through the needle assembly. In U.S. Pat. No. 4,207,870, the inventor recognized that this air blockage problem prevented the blood from flowing through the intravenous needle to a point where it could be seen by a user. In this patented device, a porous vent means is provided in conjunction with a bypass valve whereby air inside the needle assembly is allowed to pass out of this venting means during the initial stages of the blood collection procedure. However, the venting means prevents the passage of blood therethrough.

In a previously filed patent application entitled "Multiple Sample Needle With Vein Entry Indicator" by Joseph Kaufman, U.S. Ser. No. 160,781, filed June 18, 1980, and assigned to the common Assignee herewith, a different type of needle structure is disclosed which employs an air-permeable, blood-impermeable porous plug mounted within an operable valve.

Although U.S. Pat. No. 4,207,870 and the Kaufman invention are most advantageous in providing the combination one-way valve and air venting means, there is still room for improvement thereover. The present invention is directed to improving such devices by providing a mechanism for purging the air from inside the needle assembly so that blood can readily flow into the assembly as it displaces the air.

SUMMARY OF THE INVENTION

The multiple sample needle assembly of the present invention is useful in collecting liquid samples from a liquid source. This needle assembly comprises a housing with a chamber therein, and cannula means in fluid communication with the chamber. This cannula means includes a first cannula adapted for insertion into a liquid source and a second cannula adapted to deliver liquid passing through the chamber to collection means. Means in the lumen of the second cannula prevents liquid, but not gas, from flowing through the second cannula. The needle assembly includes means for operably collecting liquid from the second cannula by diverting liquid away from the liquid flow preventing means.

In a preferred embodiment of the present invention, the housing has a forward end, a rearward end and a chamber within. The housing is translucent at least around the chamber so that the chamber is viewable by a user of the assembly. The first cannula extends outwardly from the forward end and is adapted for insertion into a patient. The second cannula extends outwardly from the rearward end and is adapted for penetration of an evacuated blood collection container for collection of a blood sample. A pair of spaced holes extends through the side of the outwardly extending portion of the second cannula, with these holes communicating with the lumen of the second cannula. In the lumen of the second cannula is an air-permeable, blood-impermeable porous plug located in the space between the two holes. A resilient, slidable valve on the exterior of the second cannula normally covers one of the holes to prevent blood from flowing out of the second cannula when in the closed position. This valve is slidable to an open position and includes means for allowing the blood to flow out of the hole located closer to the chamber and then back through the second hole whereby blood is collected from the second cannula.

From the structural standpoint, the multiple sample needle assembly of the present invention is notably different from prior devices intended for the same purposes. In particular, the present invention relies upon a liquid flow impediment directly positioned inside the second cannula. One or more side holes is provided through the second cannula so that blood or other liquids flowing therethrough can be diverted away from the liquid-impermeable impediment. Preferably, a slidable sleeve valve is employed in combination with this side hole in order to control the flow of liquid which is diverted away from the liquid impediment. In prior art devices, particularly those discussed above, the liquid-impermeable member is located inside the chamber. By the structure which the present invention reveals, the chamber is free from valves or liquid-impermeable plugs. As a result, the user can better visualize the blood which enters the chamber during the venipuncture procedure. By employing a gas-permeable plug member in the second cannula, the present invention allows air to escape from the assembly when blood is filling the chamber, thereby eliminating any air block which would otherwise occur but for the gas-permeable element. Most advantageously, in the multiple sample blood collection procedure, the present invention prevents blood from leaking during the change of blood collection containers while the needle assembly remains inserted in the patient. The present invention provides for automatic flow control so that blood is prevented from leaking out of the chamber after a filled blood collection container is removed from the assembly. Other advantages are offered as well.

BRIEF DESCRIPTION OF THE DRAWINGS

FIG. 3 is an enlarged cross-sectional view of an alternate embodiment of the multiple sample needle assembly;

FIG. 6 is a cross-sectional view taken along line 6—6 of FIG. 1 with the components in an assembled condition as they would appear during use;

FIG. 8 is a cross-sectional view similar to the view of FIG. 4 but illustrating an alternate embodiment of the invention with the valve in the closed condition.

DETAILED DESCRIPTION

Figure 1:
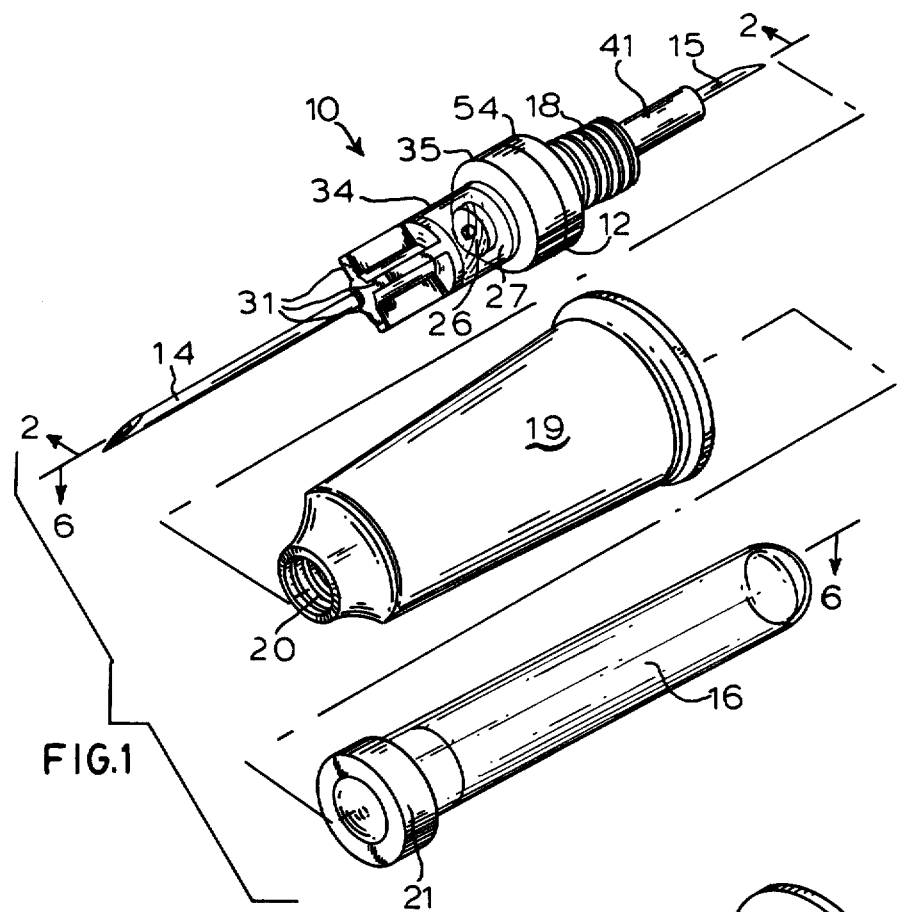
FIG. 1 is an exploded perspective view illustrating the preferred multiple sample needle assembly, a holder for an evacuated container and an evacuated blood collection container for use in obtaining blood samples from a patient.

While this invention is satisfied by embodiments in many different forms, there is shown in the drawings and will herein be described in detail preferred embodiments of the invention, with the understanding that the present disclosure is to be considered as exemplary of the principles of the invention and is not intended to limit the invention to the embodiments illustrated. The scope of the invention will be measured by the appended claims and their equivalents.

Adverting to the drawings, particularly to FIG. 1, there is illustrated the preferred embodiment of a multiple sample needle assembly 10. The basic external components of needle assembly 10 include a housing 12, a first needle cannula 14 adapted for insertion into a patient and a second needle cannula 15 at the opposite end of housing 12, the second needle cannula adapted for penetration of an evacuated container 16 for collection of a blood sample. Housing 12 includes a threaded portion 18 adjacent second cannula 15 onto which a container holder 19 is threaded by its internal mating threads 20 at the forward end of the holder. Evacuated container 16 slides into holder 19 so that second needle cannula 15 can penetrate the penetrable stopper 21 at the forward end of the evacuated container. These general aspects of multiple sample blood collections in this type of structure are well known to those skilled in this art.

Figure 2:
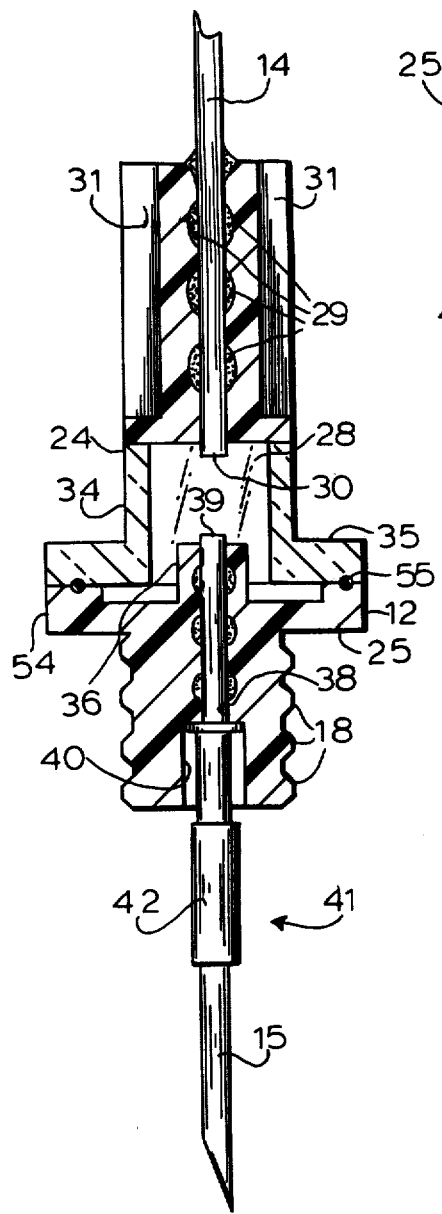
FIG. 2 is an enlarged cross-sectional view of the multiple sample needle assembly taken along line 2—2 of FIG. 1.
Figure 4:
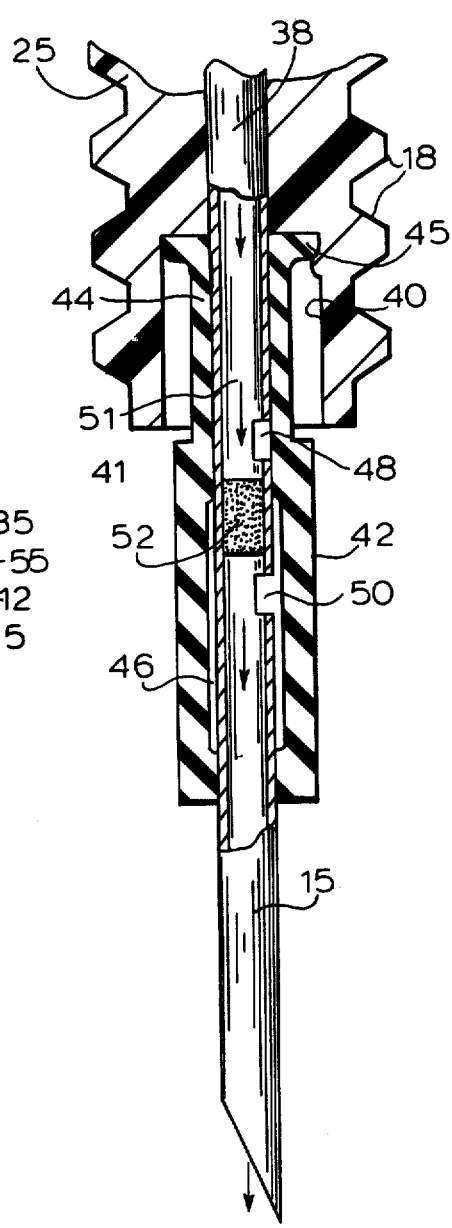
FIG. 4 is a further enlarged cross-sectional view of the valve area of the embodiments of either FIGS. 2 or 3 illustrated in the normal, closed condition so that no blood flows through the cannula.

In FIGS. 2 and 4 the detailed construction of needle assembly 10 is illustrated. Housing 12 has a forward end 24 and a rearward end 25, these ends being preferably separable to facilitate manufacture or interchangeability of components, while also being able to form the chamber within the housing. Forward end 24 is preferably cylindrically shaped and has a large bore extending into and partially through its body. This bore serves as a chamber 28 within housing 12 after the components are assembled. At the other end of this section a smaller bore 29 is included which is generally sized to fit needle cannula 14 therein. Needle cannula 14 is positioned in bore 29 so that its interior end 30 preferably lies slightly within chamber 28, thereby communicating therewith. The pointed end of needle cannula 14 extends outwardly from forward section 24. Once the needle cannula is in position it can be suitably affixed, such as by adhesive means or the like.

Forward end 24 of the housing also includes a number of longitudinal ribs 31 surrounding the outwardly extending cannula. A needle shield (not shown) generally covers the outwardly extending needle cannula and includes mating internal ribs within. The mating ribs between needle shield and needle assembly allow the user to facilitate the insertion or removal of the needle assembly into the tube holder. A portion 34 of the forward end surrounding chamber 28 is preferably smooth and translucent or transparent so that a user of this assembly can view the interior of the housing. In many situations, it may be preferable to make the entire forward end, and even possibly the rearward end, out of translucent or transparent material for ease of manufacture and to minimize the different types of materials which may be used in this assembly. Translucent rigid plastic is the most desirable material for inclusion in this assembly. Various sealed windows, ports or other means for a user to view the contents of the chamber are within the purview of this invention. It is preferable that such window or port be sealed so that any blood which enters chamber 28 upon the needle entering the vein will not escape from this assembly. Forward end 24 also includes an annular flange 35 which serves to provide a surface for joining the two portions of the housing together upon assembly. Once again, suitable fastening means, such as adhesives or the like may be used to secure the two portions of the housing together.

Rearward end 25 includes a short protruding portion 36, which is generally cylindrically shaped. This protruding portion is provided in this embodiment to add additional support to the interior end of second needle cannula 15 which is associated with the rearward end. At the opposite side of this rearward end, external threads 18 are provided as previously mentioned as a connection mechanism to the tube holder. A bore 38 extends through the rearward end of the housing. This bore is sized to accept the diameter of second needle cannula 15 so that the interior end 39 of the second needle cannula extends into chamber 28 to be in fluid communication therewith when the forward and rearward ends are mated together. Second needle cannula 15 may be suitably affixed in position inside bore 38 such as by adhesive means or the like. A larger bore 40 extends into rearward end 25 a short distance and communicates with bore 38. A sleeve valve 41 is slidably positioned over the outwardly extending portion of second needle cannula 15. Sleeve valve 41 includes a thicker-wall portion 42, a thinner-wall portion 44 and a flange 45 at the end of the thinner portion. This sleeve valve is oriented so that flange 45 and the thin wall portion thereof slide into bore 40 with flange 45 abutting against the interior portion of the rearward end of the housing. In addition, thick wall portion 42 includes a cavity portion 46 therein. Sleeve valve 41 is selected so that it has an inside diameter, except for the cavity portion, which provides an interference fit with the outside diameter of second needle cannula 15. However, cavity 46 has a diameter greater than the inside diameter of the sleeve which provides the normal interference fit with the outside of the cannula. The functional difference between these diameters will become evident with the description of the use of the present invention hereinafter.

As more clearly seen in FIG. 4, there is a pair of spaced holes 48 and 50 through the side of the outwardly extending portion of second needle cannula 15. Resilient sleeve valve 41 in its relaxed, normal condition covers both of the aforementioned holes; however, while both of these holes may be covered by the tightly fitting inner diameter of the sleeve, it is preferable to only cover hole 48 which is closer to the chamber within the housing. Thus, sleeve valve 41 provides a normally fluid-tight contact over hole 48. At the same time, cavity 46 surrounds hole 50 so that the valve is not in fluid-tight contact with hole 50.

Positioned in lumen 51 of second needle cannula 15 is a gas-permeable, liquid-impermeable porous member 52; preferably this member is a porous plug adapted to be air-permeable but blood-impermeable. Plug 52 is positioned so that it lies in the space between holes 48 and 50. Therefore, blood traveling down second needle cannula 15 is impeded by the blood-impermeable characteristics of porous plug 52 so that no blood can exit from the distal, pointed end of the second needle cannula. However, the air-permeability characteristics of porous plug 52 allow air inside chamber 28 and the second needle cannula to pass freely therethrough and exit from the distal end of the second cannula.

To facilitate the joining of the rearward and forward ends of the housing, an annular flange 54 is provided on the rearward end of the housing. To assure proper fluid flow through the housing, an annular, elastomeric ring 55 may be included in this embodiment between flanges 35 and 54. Upon assembling the forward end and the rearward end together, respective flanges 35 and 54 are secured together by appropriate fastening means, such as adhesives or the like.

Sleeve valve 41 is fabricated so that thinner-wall portion 44 is compressible against rearward end 25 when the valve is slid thereagainst, as will be explained hereinafter. The thicker-wall portion of sleeve valve 41 embodies cavity 46 and is not intended to be compressed in the axial direction as is the thinner-wall portion. Furthermore, cavity 46 has a longitudinal length which is sufficient to span both of holes 48 and 50 when the sleeve valve is slid inwardly toward the rearward end. While many materials may be employed to fabricate the sleeve valve, it is preferred that elastomeric material be used.

With respect to porous plug 52, it is preferred that it be made of porous material, one such material being sintered polyethylene having a general pore rating of about 10 microns.

Before turning to the operability of the present invention, an alternative construction of the needle cannulae is depicted in FIG. 3. In this alternative embodiment, multiple sample needle assembly 60 embodies virtually all of the same elements and features as illustrated in FIG. 2 so that corresponding elements have the same numerical designations followed by the suffix "a." However, instead of two dissociated cannulae as provided in the embodiment of FIG. 2, the alternative embodiment of FIG. 3 utilizes a single, preferably unitary cannula 61 extending through housing 12a. A first cannula portion 14a extends outwardly from forward end 24a; a second cannula portion 15a extends outwardly from rearward end 25a. A common fluid access hole 62 extends through a central region of cannula 61 so as to be in fluid communication with chamber 28a. In the embodiment of FIG. 3, blood will flow through access opening 62 to fill chamber 28 when sleeve valve 41a is closed. This will provide the user with a visual indication that successful venipuncture has been made.

Figure 5:
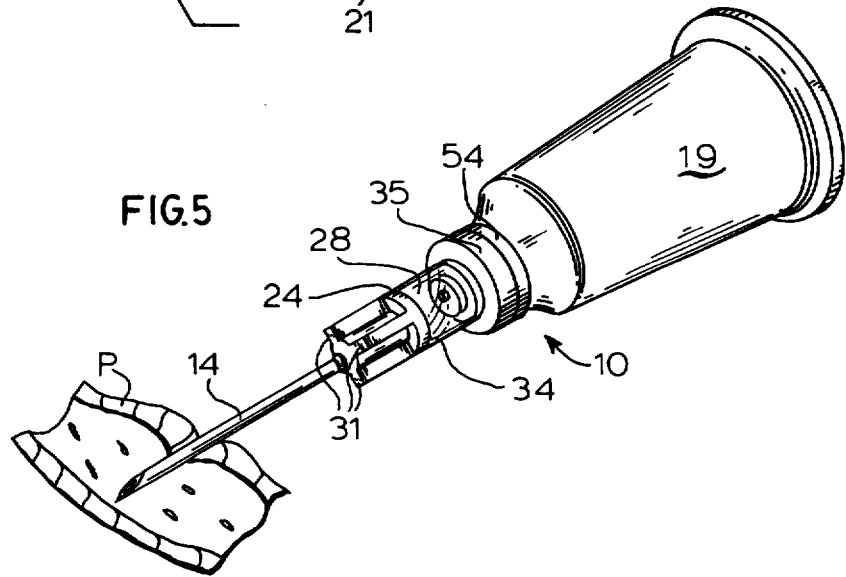
FIG. 5 is a perspective view of the needle assembly connected to a holder inserted into a patient so that a user can view same for indication of vein entry.

Turning now to FIG. 5, the preferred needle assembly 10 (or, alternatively, needle assembly 60) is illustrated connected to multiple sample holder 19. Cannula 14, extending from forward end 24, is shown inserted into a patient P during the venipuncture procedure. At this time, the needle assembly is in the normal, static condition so that the sleeve valve (not shown in FIG. 5) is in liquid-tight contact over hole 48 as previously described. Under normal tourniquet pressure, blood from the patient is forced through cannula 14 into forward end 24 of the housing and then into chamber 28. The entering blood then forces any air which may be initially inside chamber 28 out through porous plug 52, which is air-permeable, but blood-impermeable. The air exits from the second cannula at the open distal end thereof. Blood fills chamber 28 by flowing through first needle cannula 14 and out of interior opening 30, as illustrated in FIG. 2, or out of access opening 62, as illustrated in FIG. 3, if that embodiment is being utilized. With at least forward end 24, or a portion thereof, such as wall portion 34, being translucent, the user of this needle assembly can then view the blood as it enters chamber 28. As soon as the user sees the blood in the chamber, it serves as an indication that vein entry has been made. Conversely, if the user does not see blood flow into the chamber after needle cannula 14 has been inserted into the patient, it can be assumed that unsatisfactory vein entry has been accomplished. With this feature, the user does not have to attach an evacuated blood collection container to second needle cannula 15 inside holder 19 until vein entry indication has been determined. No blood will flow through second needle cannula 15 inasmuch as blood-impermeable plug 52 and sleeve valve 41 prevent the flow of blood out of the second needle cannula. Once the user is satisfied that vein entry has been made, evacuated blood collection container 16 is slid into holder 19 so that second needle cannula 15 penetrates penetrable stopper 21. This combination is illustrated in FIG. 6.

Figure 7:
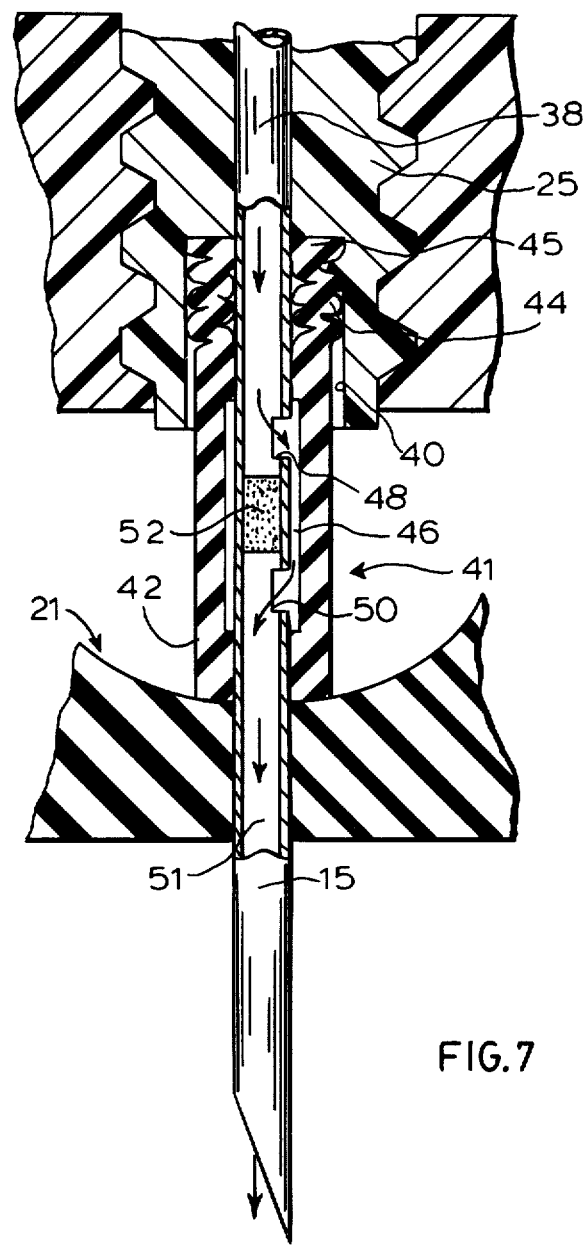
FIG. 7 is an enlarged cross-sectional view of the valve area of the invention illustrating the valve in the open condition so that blood flows through the cannula.

Referring now to FIG. 6, evacuated blood collection container 16 is illustrated fully inserted into holder 19 so that second needle cannula 15 has pierced penetrable stopper 21 with its leading edge inside the blood collection container for delivery of blood thereto. As needle cannula 15 is passing through penetrable stopper 21, resilient sleeve valve 41 is slid along the outside surface of the needle cannula and compressed toward rearward end 25. An enlarged view of compressed sleeve valve 41 is illustrated in FIG. 7. It can be seen that thin wall portion 44 compresses in accordion-like fashion inside bore 40 against the rearward end of the needle assembly. On the other hand, thick wall portion 42 does not fold or become compressed, but merely slides toward the rearward end of the assembly. This sliding effect of thick wall portion 42 places cavity 46 over both of holes 48 and 50 so that neither hole is being blocked in liquid-tight fashion. As a result, the blood in second needle cannula 15, the flow of which had been blocked by blood-impermeable plug 52, is diverted around or away from this intended obstacle. Thus, as illustrated in FIG. 7, blood by-passes plug 52 by flowing through hole 48 and into cavity 46. Blood then flows from the cavity through hole 50 back inside lumen 51 of the second needle cannula for continued flow therethrough. The blood flows out of the distal open end of the second needle cannula for collection in the blood collection container.

Once blood has been collected in the blood collection container, this filled container is removed from holder 19 while needle cannula 14 remains inserted in the vein of the patient. Removal of the blood collection container also removes the compressive force against slidable sleeve 41 causing the sleeve to slide outwardly to once again assume the position as illustrated in FIG. 4. This represents the closed valve position thereby preventing blood from flowing out of second needle cannula 15. This movement of the sleeve valve automatically causes a prevention of blood from flowing out of the second needle cannula. No blood will leak out of this assembly especially during the time period between changes of evacuated blood collection containers. Therefore, the blood will flow from the patient's vein and into chamber 28 until the next blood collection container is inserted into the holder to repeat the inward, compressive movement of the slidable valve as previously described. Once multiple samples of blood have been taken, needle cannula 14 is removed from the patient, whereupon the entire needle assembly is discarded.

Figure 9:
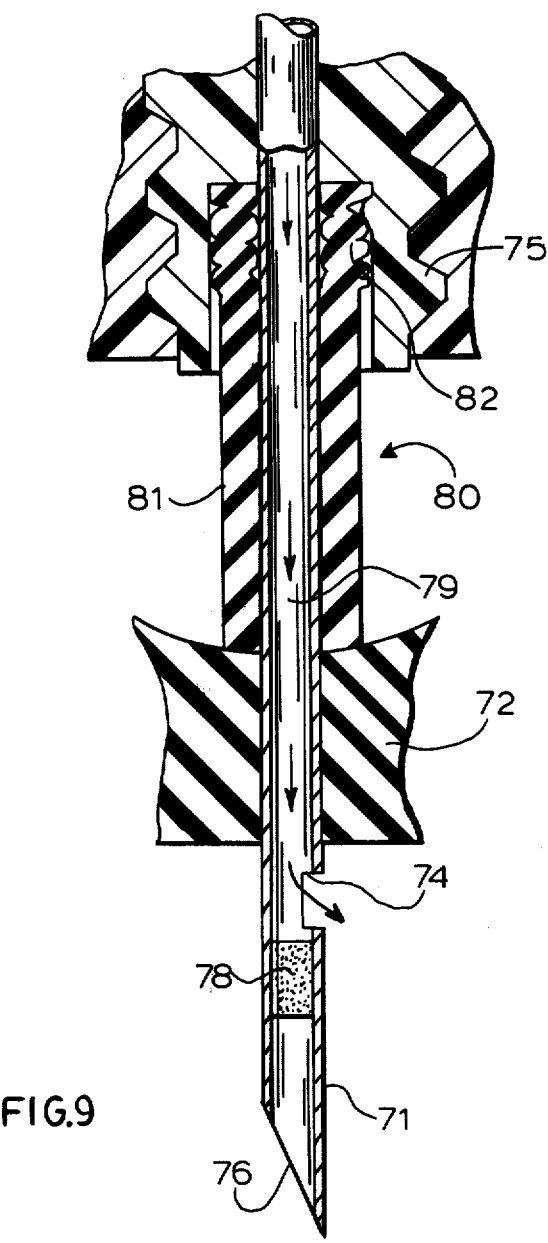
FIG. 9 is a cross-sectional view illustrating the embodiment of FIG. 8 when the vale is in the open position with blood flowing through the cannula.

While a number of embodiments can be conceived which fall within the purview of the present invention, FIGS. 8 and 9 illustrate an alternative valving arrangement to prevent blood from flowing out of the cannula during the closed valve position, while allowing air to escape for purging purposes. In the alternative embodiment of FIG. 8, multiple sample needle assembly 70 is substantially similar in most respects to the previously described embodiments, except that needle cannula 71, intended to pierce penetrable stopper 72 of a blood collection container, includes only on side hole 74 therethrough. This side hole is located in needle cannula 71 substantially spaced from rearward end 75 of the needle assembly and closer to the open, distal end 76 of the needle cannula. The gas-permeable, liquid-impermeable porous plug 78 is positioned inside lumen 79 so that it lies between side hole 74 and open end 76. Sleeve valve 80 is substantially similar to sleeve valve 41 previously described, except that it is somewhat longer in order to cover side hole 74 in liquid-tight contact. Sleeve valve 80 also need not include an interior cavity such as found in previously described sleeve valve 41. Also, whereas sleeve valve 80 is illustrated as having a thicker wall portion 81 and a thinner wall portion 82, this is merely a preferable arrangement since the wall thickness of the sleeve could be uniform throughout.

With sleeve 80 in the position illustrated in FIG. 8, representing the closed condition, air inside the needle assembly is permitted to pass through air-permeable plug 78, whereas blood is prevented from flowing therethrough. Also, no blood will flow out of side hole 74 since sleeve 80 effectively closes this hole. FIG. 9 illustrates sleeve valve 80 in the compressed condition, similar to that of FIG. 7. Needle 71 has passed through penetrable stopper 72 so that side hole 74 is inside the blood collection container. Sleeve valve 80 has been slid so that it is compressed toward rearward end 75 of the needle assembly. With side hole 74 exposed, blood inside lumen 79 will flow out of side hole 74 directly into the blood collection container. It can be seen in FIG. 9 that blood is diverted away from plug 78 so that it flows out of side hole 74, rather than through the distal open end of the needle cannula. Once the blood collection container is filled, it is removed from the holder whereupon sleeve valve 80 slides back to the condition illustrated in FIG. 8. This effectively prevents blood from flowing out of the cannula during the time period for change of the blood collection containers.

Thus, the multiple sample needle assembly of the present invention controls the flow of blood or other liquids therethrough. Blood is prevented from leaking out of this assembly particularly during change of blood collection containers during the multiple sampling procedure. Furthermore, the present invention provides a visual indicator to the user so that a quick determination can be made when the vein has been entered for collection of blood therefrom. These aforementioned features contribute to the efficient use of this type of assembly in the multiple sample collection procedure.

What is claimed is:

1. A multiple sample needle assembly for determining vein entry when collecting blood samples from a patient comprising:
   a housing have a forward end, a rearward end and a chamber within, said housing being translucent at least around the chamber so that said chamber is viewable by a user of said assembly;
   a first cannula in fluid communication with said chamber extending outwardly from said forward end adapted for insertion into a patient;
   a second cannula in fluid communication with said chamber extending outwardly from said rearward end adapted for penetration of an evacuated container for collection of a blood sample;
   a pair of spaced holes through the side of the outwardly extending portion of the second cannula, said holes communicating with the lumen of said second cannula;
   an air-permeable, blood impermeable porous plug positioned in the lumen of said second cannula in the space between said holes;
   a resilient, slidable valve on the exterior of said second cannula; said resilient slidable valve being slidable on said second cannula from a first position covering at least one of said pair of holes for preventing blood from flowing out of said second cannula to a second position allowing blood to flow out of said one hole; and means in said resilient slidable valve for allowing blood to flow out of said one hole and back into said second cannula through the other of said pair of holes whereby blood is collected from said second cannula, into a container attached thereto.

2. The assembly of claim 1 wherein said valve is a sleeve in fluid-tight, but slidable, contact on said second cannula.

3. The assembly of claim 2 wherein said sleeve covers said hole located closer to said chamber in fluid-tight contact when in the first position thereof.

4. The assembly of claim 2 wherein said sleeve includes at least a portion thereof with an inside diameter in interference fit with one outside diameter of said second cannula for covering at least one of said holes in fluid-tight contact.

5. The assembly of claim 4 wherein said means for allowing blood flow includes a longitudinally extending cavity inside said sleeve having a diameter greater than said interference fit diameter, said cavity having a longitudinal extent along said sleeve which is sufficiently long to span both of said holes when said sleeve is slid to said second position, whereby blood is allowed to by-pass said plug by flowing through the hole located closer to said chamber into and along said cavity and then back into said other hole for continued flow through said second cannula and collection therefrom.

6. The assembly of claim 5, wherein said sleeve further comprises
    (a) a longitudinally extending sleeve portion extending from said cavity containing portion and having a thinner wall than the remainder of said sleeve;
    (b) said longitudinally extending thinner walled portion of said sleeve being on the end thereof nearest said chamber; and
    (c) said thinner walled portion being compressible along said second cannula against said rearward end.

7. The assembly of claims 2 or 5 wherein said sleeve is an elastomeric material.

8. The assembly of claim 1 wherein said first and said second cannulae are joined together in said chamber and both of said cannulae communicate with said chamber through a common access opening.

9. The assembly of claim 1 wherein said porous plug is made of sintered polyethylene.

10. The assembly of claim 1 wherein the housing includes means for connecting a holder for an evacuated container.

11. The assembly of claim 10 which further includes a holder for an evacuated container connected to said housing.

12. The assembly of claim 1 wherein said first and said second cannulae are joined together at the ends thereof inside said chamber to form an integral unitary cannula means with a common fluid access for communication with said chamber.

13. A multiple sample needle assembly for determining vein entry when collecting blood samples from a patient comprising:

a translucent housing having a forward end, a rearward end and a chamber within, said chamber being viewable by a user of said assembly;

a first cannula in fluid communication with said chamber extending outwardly from said forward end adapted for insertion into a patient;

a second cannula in fluid communication with said chamber extending outwardly from said rearward end adapted for penetration of an evacuated container for collection of a blood sample;

a pair of spaced holes through the side of the outwardly extending portion of the second cannula with one hole spaced closer and one further from said chamber, said holes communicating with the lumen of said second cannula;

an air-permeable, blood-impermeable porous plug positioned in the lumen of said second cannula in the space between said holes; and a resilient, slidable, elastomeric sleeve on the exterior of said second cannula slidable from a first position covering at least one of said holes in fluid-tight contact to prevent any blood collected from a patient by said first cannula from flowing out of said second cannula to a second position, said sleeve having a longitudinally extending portion thereof with an inside diameter in interference fit with the outside diameter of said second cannula for providing said fluid tight contact and also having a longitudinally extending portion with a cavity therein with a diameter greater than said interference fit diameter, said cavity being sufficiently long to span both of said holes, said sleeve being slidable toward said rearward end to said second position whereby said cavity is positioned over said holes so that blood is allowed to by-pass said plug by flowing through the hole located closer to said chamber, into and along said cavity and then back into said other hole for continued flow through said second cannula and collection therefrom, said sleeve having a longitudinally compressible portion, not containing said cavity at the end thereof adjacent said rearward end, which is compressible against said rearward end when slid thereagainst during the collection of blood from the second cannula.

* * * * *